United States Patent [19]

Benoit et al.

[11] Patent Number: 5,395,845
[45] Date of Patent: Mar. 7, 1995

[54] PYRETHRINOID ESTERS OF THIAZOLE ALCOHOLS

[75] Inventors: Marc Benoit, Roquevaire; Jean-Pierre Demoute, Neuilly Plaisance; Christian Wehrey, Fontenay Sous Bois, all of France

[73] Assignee: Roussel-Uclaf, France

[21] Appl. No.: 15,355

[22] Filed: Feb. 8, 1993

[30] Foreign Application Priority Data

Feb. 12, 1992 [FR] France .................. 92 01556

[51] Int. Cl.$^6$ .................. C07D 777/30; A01N 43/78
[52] U.S. Cl. .................. 514/365; 514/369; 548/186; 548/204
[58] Field of Search .............. 548/186, 204; 514/365, 514/369

[56] References Cited

FOREIGN PATENT DOCUMENTS 0041021 2/1981 France.
2500451 8/1982 France.
2719561 11/1977 Germany.

OTHER PUBLICATIONS

A publication of Chemical Abstracts Service vol. 78, No. 17, Apr. 30, 1973–Rapport de Recherche No. 01556 Search Report.

Primary Examiner—Robert Geastl
Attorney, Agent, or Firm—Bierman and Muserlian

[57] ABSTRACT

In all possible stereoisomer forms and mixtures thereof of the formula

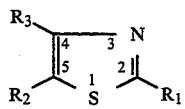

wherein one of $R_1$, $R_2$ or $R_3$ is:

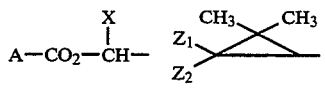

11 Claims, No Drawings

PYRETHRINOID ESTERS OF THIAZOLE ALCOHOLS

STATE OF THE ART

Related prior art include Kaoru, et al., Chem. Abs., Vol. 78, No. 17 (1973), No. 111,193w, U.S. Pat. No. 4,450,169, E.P.A. No. 0,041,021 and DE-A-2,719,561.

OBJECTS OF THE INVENTION

It is an object of the invention to provide the novel esters of formula I and a process and intermediates for their preparation.

It is another object of the invention to provide novel pesticidal compositions and a novel method of combatting pests.

These and other objects and advantages of the invention will become obvious from the following detailed description.

THE INVENTION

The novel compounds of the invention are compounds in all possible stereoisomer forms and mixtures thereof of the formula

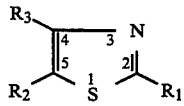

I wherein one of $R_1$, $R_2$ or $R_3$ is:

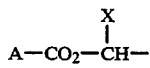

X is hydrogen, C≡N, alkyl, alkenyl and alkynyl of up to 4 carbon atoms and
either A is:

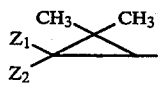

wherein $Z_1$ is hydrogen and
either $Z_2$ is:

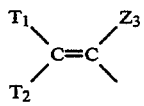

wherein $Z_3$ is hydrogen or halogen and $T_1$ is selected from the group consisting of hydrogen, halogen, alkoxy and alkyl of 1 to 8 carbon atoms optionally substituted by a member of the group consisting of halogen, mono-, di- or trifluoromethyl, cyano and phenyl optionally substituted by halogen and $T_2$ is selected from the group consisting of hydrogen, halogen, alkoxy of 1 to 8 carbon atoms optionally substituted by halogens or alkyl of 1 to 8 carbon atoms substituted by a member of the group consisting of halogen, mono-, di- or trifluoromethyl, cyano and phenyl optionally substituted by halogen or $T_1$ and $T_2$ form together a cycloalkyl of 3 to 6 carbon atoms or:

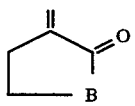

wherein B is oxygen or sulfur;
or $Z_2$ is:

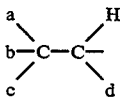

wherein a, b, c and d, individually are halogen,
or $Z_2$ is:

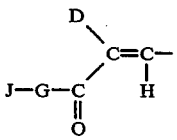

wherein D is selected from the group consisting of hydrogen or halogen, alkoxy of 1 to 8 carbon atoms, G is oxygen or sulfur and J is optionally unsaturated alkyl or cyclo alkyl of up to 8 carbon atoms optionally substituted by at least one functional group, aryl of 6 to 14 carbon atoms optionally substituted by at least one functional group and a heterocyclic optionally substituted by at least one functional group,
or A is:

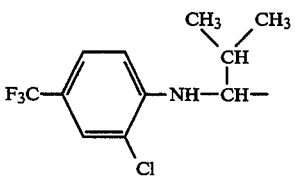

or:

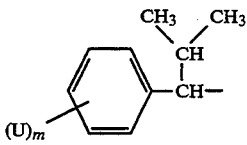

wherein U in any position on the benzene is selected from the group consisting of halogen, alkyl of 1 to 8 carbon atoms and alkoxy of 1 to 8 carbon atoms, m is 0, 1 or 2 and when m is 2, the U substituents may be different and the other two of $R_1$, $R_2$ and $R_3$ which are not:

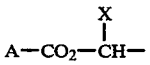

are individually selected from the group consisting of hydrogen, halogen, alkyl, alkenyl and alkynyl of up to 8 carbon atoms optionally substituted by at least one halogen, hydroxyl, O-alkyl, O-alkenyl or O-alkynyl, $CO_2$-alkyl, $CO_2$-alkenyl, $CO_2$-alkynyl, $S(O)_n$-alkyl, $S(O)_n$-alkenyl or $S(O)_n$-alkynyl, n is 0, 1 or 2, of up to 8 carbon atoms optionally substituted by at least one halogen, aryl, O-aryl or thioaryl of up to 14 carbon atoms optionally substituted by at least one member of the group consisting of halogen, alkyl, alkenyl and alkynyl of up to 8 carbon atoms optionally substituted by at least one halogen and esterified, etherified or free hydroxy, heteroaryl and heteroaryloxy, —C≡N, —NH₂ and —NO₂.

When X is alkyl, it is preferably methyl or ethyl. When X is alkynyl, it is preferably ethynyl.

When $T_1$, $T_2$ or $Z_3$ are halogen, it is preferably fluorine, chlorine or bromine. When $T_1$ or $T_2$ is alkyl or alkoxy, it is preferably methyl, ethyl, propyl, methoxy, ethoxy or propoxy.

a, b, c and d preferably are chlorine or bromine. When D is halogen, it is preferably fluorine, chlorine or bromine. When J is alkyl of 1 to 8 carbon atoms substituted by at least one functional group, the alkyl may be methyl, ethyl, propyl, iso-propyl, butyl, isobutyl or tert-butyl substituted by a functional group of the European Application published under the number 50534.

J can also be alkyl substituted by aryl, particularly an optionally substituted phenyl. When J is alkyl substituted by one or more functional groups, there can be mentioned as preferred values of J:

—(CH₂)$_{n1}$—C(Hal)₃ in which n1 is an integer from 1 to 8 and Hal is halogen, for example the —CH₂—CCl₃, —CH₂—CF₃, —CH₂—CH₂-CCl₃ or CH₂—CH₂—CF₃;

—(CH₂)$_{n2}$—CH(Hal)₂ in which Hal is defined as above and n2 is a number from 0 to 8, for example —CH₂—CHCl₂, —CH₂—CHF₂ or —CHF₂;

—(CH₂)$_{n1}$—CH₂(Hal) in which n1 and Hal are defined as above for example —CH₂—CH₂Cl or —CH₂—CH₂F, —C(CHal₃)₃ in which Hal is defined as above, for example —C(CF₃)₃ or —C(CF₃)₂—CCl₃, —C(CF₃)₂—CH₃, —C(CH₃)₂—CF₃ or —C(CH₃)(CF₃)—CH₂—CH₃, —CH(CF₃)—CH₃ or —CH(CF₃)₂, —C(CH₃)₂—CN, —CH(CH₃)—CN or —(CH₂)$_n$—CN in which n is defined as previously, —CH(CN)—C(Hal)₃ in which Hal is defined as previously, for example —CH(CN)—CCl₃

—(CH₂)$_{n1}$—OR$_a$, in which n1 is defined as previously and R$_a$ is hydrogen or alkyl of 1 to 8 carbon atoms, for example —CH₂—OCH₃, —CH₂—CH₂—O—CH₃, —CH₂—CH₂—O—CH₂—CH₃ or —CH₂—CH₂—OH;

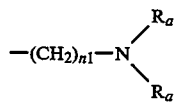

in which n1 and R$_a$ are defined as previously and the two R$_a$ can be different, for example:
—CH₂—CH₂—NH—CH₃, —CH₂—CH₂—N(CH₃)₂ or —CH₂—CH₂—N(CH₃)—CH₂—CH₃;

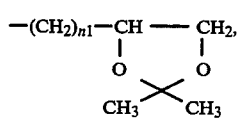

in which n1 is defined as previously, for example:

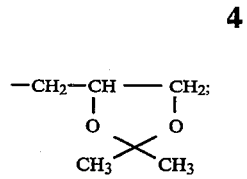

—(CH₂)$_{n1}$—CH(OH)—CH₂—OH
in which n1 is defined as previously, for example:
—CH₂—CH(OH)—CH₂—OH; —(CH₂)$_{n1}$—O—THP
in which n1 is defined as previously and THP is 2-tetrahydropyrannyl, for example:
—CH₂—O—THP or —CH₂—CH₂—O—THP;

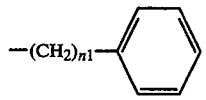

in which n1 is defined as previously, for example benzyl or phenethyl;

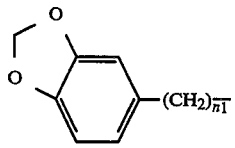

in which n1 is defined as previously, for example:

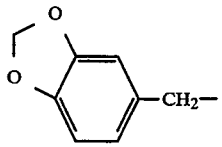

When J is an optionally substituted aryl, it is preferably optionally substituted phenyl. When J is heterocyclic, it is preferably pyridyl, furyl, thienyl, oxazolyl or thiazolyl.

In the definition of the $R_1$, $R_2$ and $R_3$, when these are not

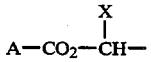

halogen preferably is fluorine, chlorine or bromine, alkyl, alkenyl and alkynyl preferably are methyl, ethyl, isopropyl, n-butyl, isobutyl, tert-butyl, vinyl, allyl, ethynyl or propynyl, alkyl substituted by halogen, preferably is —CF₃, —CHF₂, —CHCl₂, —CH₂Br, —CH₂F or

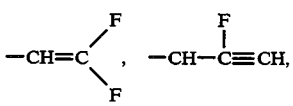

aryl preferably is phenyl optionally substituted by one or more halogen, for example pentafluorophenyl or phenyl substituted by one or more CF₃ or OCF₃, heteroaryl is for example thienyl, furyl, pyridyl, thiazolyl or tetrazolyl.

Among the preferred compounds of formula I are those wherein one of $R_1$, $R_2$ and $R_3$ is hydrogen,
those wherein one of $R_1$, $R_2$ or $R_3$ is:

$$A-CO_2-\overset{X}{\underset{}{C}H}-$$

in the 4-position
  those wherein one of $R_1$, $R_2$ or $R_3$ is hydrogen in the 5-position,
  those wherein one of $R_1$, $R_2$ or $R_3$ is alkyl of 1 to 4 carbon atoms optionally substituted by one or more halogens,
  those wherein one of $R_1$, $R_2$ or $R_3$ is O-alkyl or S-alkyl optionally substituted by one or more halogens,
  those wherein alkyl, O-alkyl or S-alkyl is substituted by one or more fluorines,
  those wherein one of $R_1$, $R_2$ or $R_3$ is $-CF_3$,
  those wherein one of $R_1$, $R_2$ or $R_3$ is $-OCHF_2$,
  those wherein X is ethynyl or hydrogen and those wherein one of $R_1$, $R_2$ or $R_3$ is:

$$\underset{Cl}{\overset{CF_3}{\diagdown}}C=CH-\overset{CH_3}{\diagup}\underset{}{\diagdown}\overset{CH_3}{\diagdown}$$

The novel process of the invention for the preparation of a compound of formula I comprises reacting an acid of the formula $$ACOOH \qquad II$$

or a functional derivative thereof wherein A is as defined above with an alcohol of the formula $$\underset{R'_2}{\overset{R'_3}{\diagdown}}\underset{S}{\diagup}\overset{N}{\diagdown}R'_1 \qquad III$$

in which one of $R'_1$, $R'_2$ or $R'_3$ is:

$$-\overset{X}{\underset{H}{C}}-OH$$

X has the above definition and the other two Rs have the same meaning as $R_1$, $R_2$ and $R_3$ with the exception of:

$$A-CO_2-\overset{X}{\underset{}{C}H}-$$

a functional derivative of the alcohol of formula III, to obtain the corresponding compound of formula I.

The functional derivative of the acid used is preferably an acid chloride. When the acid of formula II is reacted with the alcohol, the operation is preferably carried out in the presence of dicyclohexylcarbodiimide.

The acids of formula II are known products used in the synthesis of pyrethrinoid compounds. The alcohols of formula III are products generally known and can be prepared for example according to the processes described in the European Patent Application No. 402,246 or in French Patents No. 2,647,787, No. 2,289,189, No. 2,500,451 and No. 2,500,452. Some alcohols of formula III whose preparation is given hereafter are new products and are themselves a subject of the present invention.

The compounds of formula I have useful properties which allow their use for combatting parasites and it may be for example used for combatting parasites of vegetation, parasites of premises and parasites of warm-blooded animals. It is thus that the products of the invention can be used for combatting parasitic insects, nematodes and acaridae of vegetation and animals. Preferred is the use of the compounds of formula I for combatting parasites of vegetation, parasites of premises and parasites of warm-blooded animals.

The products of formula I can also be used for combatting insects and other parasites of the soil, for example Coleoptera such as Diabrotica, *click beetles* and May beetle grubs, Myriapoda such as *scutigeridae* and *blanjules*, Diptera such as *cecydomia* and Lepidoptera such as *owlet moths*. They are used at doses between 10 g and 300 g of active ingredient per hectare.

The products of formula I can also be used for combatting insects in premises, for combatting particularly flies, mosquitoes and cockroaches.

The products of formula I are also photostable and not very toxic to mammals. All of these properties mean that the products of formula I correspond perfectly to the requirements of the modern agrochemical industry as they enable crops to be protected while preserving the environment.

The products of formula I can also be used for combatting parasitic acaridae and nematodes of vegetation as well as for combatting parasitic acaridae of animals, for combatting for example ticks and notably ticks of the Boophilus type, those of the Hyalomnia type, those of the Amblyomnia type and those of the Rhipicephalus type or for combatting all sorts of mites and notably the sarcoptic mite, the psoroptic mite and the chorioptic mite.

Therefore a subject of the invention is also the compositions intended for combatting parasites of warm-blooded animals, parasites of premises and of vegetation, characterized in that they contain at least one of the products of formula I defined above and notably the products of formula I of Example 1.

In particular the insecticide compositions containing as active ingredient at least one of the products of formula I are useful. These compositions are prepared by the usual processes of the agrochemical industry or the veterinary industry or the industry for products intended for animal fodder.

The compositions can be in the form of powders, granules, suspensions, emulsions, solutions, aerosol solutions, combustible bands, baits or other preparations usually employed for the use of these types of compounds.

In addition to the active ingredient, these compositions contain generally a vehicle and/or a non-ionic surfactant to ensure a uniform dispersion of the components of the mixture. The vehicle used can be a liquid, such as water, alcohol, hydrocarbons or other organic solvents, a mineral, animal or vegetable oil, a powder such as talc, clays, silicates, kieselguhr or a combustible solid. The insecticide compositions according to the invention preferably contain from 0.005% to 10% by weight of active ingredient.

According to an advantageous method for use in premises, the compositions of the invention are used in the form of fumigant compositions. The compositions of the invention can be advantageously constituted, for the non-active part, by a combustible insecticide coil, or also an incombustible fibrous substrate. In the latter case, the fumigant after incorporation of the active ingredient is placed on a heating apparatus such as an electric emanator.

In the case where an insecticide coil is used, the inert support can be, for example, pyrethrum marc compound, Tabu powder (or Machilus Thumbergii leaf powder), pyrethrum stem powder, cedar leaf powder, sawdust (such as pine sawdust), starch and coconut shell powder. The dose of active ingredient can then be, for example, 0.03 to 1% by weight. In the case where an incombustible fibrous support is used, the dose of active ingredient can then be, for example, from 0.03 to 95% by weight.

The compositions of the invention for use in premises can also be obtained by preparing a sprayable oil based on the active ingredient, this oil soaking the wick of a lamp and then being set alight. The concentration of active ingredient incorporated in the oil is, preferably, 0.03 to 95% by weight.

Also the acaricide and nematocide compositions containing as active ingredient at least one of the products of formula I are a part of the invention. The insecticide compositions of the invention, as acaricide and nematocide compositions, can optionally have added to them at least one other pesticide agent. The acaricide and nematocide compositions can be in the form of powder, granules, suspensions, emulsions, solutions.

For acaricide use, wettable powders are preferably used for foliar dusting containing 1 to 80% by weight of active ingredient or liquids for foliar spraying containing 1 to 500 g/l of active ingredient. Powders can also be used for foliar dustings containing 0.05 to 3% of active ingredient.

For nematocide use, liquids are preferably used for soil treatment containing 300 to 500 g/l of active ingredient. The acaricide and nematocide compositions of the invention are used, preferably, at doses comprised between 1 and 100 g of active ingredient per hectare.

To enhance the biological activity of the products, they can contain the standard synergists used in such a case such as 1-(2,5,8-trioxadodecyl) 2-propyl 4,5-methylenedioxy benzene (or piperonyl butoxide) or N-(2-ethyl heptyl) bicyclo[2,2-1]5-heptene-2,3-dicarboximide, or piperonyl-bis-2-(2'-n-butoxy ethoxy) ethylacetal (or tropital).

The compounds of formula I have an excellent general tolerance, and therefore are useful for combatting particularly illnesses caused by ticks and mites in man and in animals as well as to combat lice in a preventive or curative way and to combat scabies.

The products can be administered externally, by spraying, by shampooing, by bathing or painting on. The products for veterinary use can also be administered by painting on the dorsal spine according to the so-called "pour-on" method. The products of the invention can be used as biocides or as growth regulators.

Also the compositions endowed with insecticide, acaricide or nematocide activity, a second ingredient of at least one of the pyrethrinoid esters selected from the group consisting of the esters of allethrolone, of 3,4,5,6-tetrahydrophthalimidomethyl alcohol, of 5-benzyl-3-furyl methyl alcohol, of 3-phenoxybenzyl alcohol and of alpha-cyano-3-phenoxybenzyl alcohol with chrysanthemic acids, by the esters of 5-benzyl-3-furyl methyl alcohol with 2,2-dimethyl-3-(2-oxo-3-tetrahydrothiophenylidenemethyl)-cyclopropanecarboxylic acids, by the esters of 3-phenoxybenzyl alcohol and of alpha-cyano-3-phenoxybenzyl alcohol with 2,2-dimethyl-3-(2,2-dichlorovinyl)-cyclopropanecarboxylic acids, by the esters of alpha-cyano-3-phenoxy-benzyl alcohol with 2,2-dimethyl-3-(2,2-dibromovinyl)-cyclopropanecarboxylic acids, by the esters of 3-phenoxybenzyl alcohol with 2-parachlorophenyl-2-isopropyl acetic acids, by the esters of allethrolone, of 3,4,5,6-tetrahydrophthalimidomethyl alcohol, of 5-benzyl-3-furyl methyl alcohol, of 3-phenoxybenzyl alcohol, and of alpha-cyano-3-phenoxybenzyl alcohol with 2,2-dimethyl-3-(1,2,2,2-tetrahaloethyl)-cyclopropanecarboxylic acids, in which "halo" represents a fluorine, chlorine or bromine atom, it being understood that the compounds (I) can exist in all their possible stereoisomer forms as well as the acid and alcohol copulas of the above pyrethrinoid esters.

In the following examples, there are described several preferred embodiments to illustrate the invention. However, it should be understood that the invention is not intended to be limited to the specific embodiments.

EXAMPLE 1

1-[2-trifluoromethyl 4-thiazolyl] 2-propynyl [1R-[1α, 3α(Z)]] 3-(2-chloro 3,3,3-trifluoro 1-propenyl) 2,2-dimethyl cyclopropane carboxylate isomer A and isomer B 0.41 g of dicyclohexylcarbodiimide and 5 ml of methylene chloride were added at 0° C. to a solution of 0.48 g of [1R-[1α, 3α(Z)]]-3-(2-chloro 3,3,3-trifluoro 1-propenyl) 2,2-dimethyl cyclopropane carboxylic acid, 0.41 g of α-ethynyl 2-trifluoromethyl 4-thiazolemethanol, 20 ml of methylene chloride and 20 mg of 4-dimethylamino-pyridine (DMAP). The reaction mixture was stirred at 0° C. for 30 minutes and allowed to return to about 20°-25° C. After filtration, the product obtained was evaporated to dryness and the residue was chromatographed on silica eluting with a hexane-ethyl acetate mixture (9-1) to obtain 0.6 g of the desired product with a Rf=0.12.

NMR:

| H of the twinned methyls | 1.28; 1.30 and 1.32 ppm |
|---|---|
| H in position 1 and 3 of the cyclopropane | 2.06 (d, J = 8.5 Hz) and 2.22 ppm (m) |
| H of the carbon carrying the ethynyl | 6.56 ppm and 6.61 ppm (d, J = 1.5 Hz) |
| H of the ethynyl | 2.71 ppm (d, J = 1.5 Hz) |
| ethylenyl H (ΔZ) | 6.88 ppm (d, J = 9.5 Hz) |
| H in alpha position of the sulphur | 7.79 ppm and 7.80 ppm |

The corresponding R and S isomers were separated by chromatography on silica eluting with a heptane-t-butylmethylether mixture (95-5) to obtain a product A with a Rf=0.16 and a product B with a Rf=0.12.

PREPARATION OF EXAMPLE 1

α-ethynyl 2-(trifluoromethyl) 4-thiazolemethanol 11 ml of a molar solution of ethynyl magnesium bromide were added to a solution of tetrahydrofuran (THF) with 2 g of 2-(trifluoromethyl) 4-thiazolecarboxaldehyde and the reaction mixture was stirred for 30 minutes at about 20°–25° C. It was poured into a solution of ammonium chloride and extraction was carried out with methylene chloride. The extracts were dried, filtered and evaporated to dryness to obtain 2.1 g of the desired product.

Using the procedure of Example 1, the following compounds were obtained:

EXAMPLE 2

[2-(trifluoromethyl) 4-thiazolyl] methyl [1R-[1alpha, 3alpha(Z)]]-3-(3-methoxy 3-oxo 1-propenyl) 2,2-dimethyl cyclopropane carboxylate melting at 117° C.

EXAMPLE 3

[2-(trifluoromethyl) 4-thiazolyl] methyl [1R-[1α,3α(Z)]]-3-)2-chloro 3,3,3-trifluoro 1-propenyl) 2,2-dimethyl cyclopropane carboxylate with a specific rotation of $[\alpha]_D = +28°$ (c=0.35% in CHCl$_3$).

EXAMPLE 4

[2-trifluoromethyl-4-thiazolyl]-methyl [1R-[1α, 3α(E)]]-3-[2-fluoro 3-(1,1-dimethyl ethoxy) 3-oxo 1-propenyl] 2,2-dimethyl cyclopropane carboxylate with a specific rotation of $[\alpha]_D = +48°$ (c=0.35% in CHCl$_3$).

EXAMPLE 5

[2-(trifluoromethyl)-4-thiazolyl]-methyl [1R-[1α, 3α(Z)]] 2,2-dimethyl 3-[3-oxo 3-[2,2,2-trifluoro 1-trifluoromethyl-ethoxy] 1-propenyl] cyclopropane carboxylate with a specific rotation of $[\alpha]_D = +35°$ (c=0.25% in CHCl$_3$).

EXAMPLE 6

[2-trifluoromethyl-4-thiazolyl]-methyl [1R-[1α, 3α]]-3-(2,2-dichloro ethenyl) 2,2-dimethyl cyclopropane carboxylate with a specific rotation of $[\alpha]_D = +8°$ (c=0.2% in CHCl$_3$).

EXAMPLE 7

[2-pentafluorophenyl-4-thiazolyl] methyl [1R-[1α, 3α]]-3-(2,2-dichloro ethenyl) 2,2-dimethyl cyclopropane carboxylate with a specific rotation of $[\alpha]_D = -2.5°$ (c=0.9% in CHCl$_3$).

EXAMPLE 8

[2-pentafluorophenyl-4-thiazolyl] methyl [1R-[1α, 3α(Z)]]-3-(2-chloro 3,3,3-trifluoro 1-propenyl) 2,2-dimethyl cyclopropane carboxylate with a specific rotation of $[\alpha]_D = +0429$ 16° (c=0.6% in CHCl$_3$).

9

[2-pentafluorophenyl-4-thiazolyl] methyl [1R-[1α, 3α(E)]]-3-[2-fluoro 3-(1,1-dimethyl ethoxy) 3-oxo 1-propenyl] 2,2-dimethyl cyclopropane carboxylate melting at 101° C.

EXAMPLE 10

[2-(2,3,4,5,6-pentafluorophenyl)-4-thiazolyl] methyl [1R-[1α, 3α(Z)]]-3-(3-methoxy 3-oxo 1-propenyl) 2,2-dimethyl cyclopropane carboxylate with a specific rotation of $[\alpha]_D = 42.5°$ (c=0.6% in CHCl$_3$).

EXAMPLE 11

[2-pentafluorophenyl-4-thiazolyl] methyl [1R-[1α, 3α(Z)]]2,2-dimethyl-3-[3-oxo 3-[2,2,2-trifluoro 1-trifluoromethyl-ethoxy] 1-propenyl] cyclopropane carboxylate with a Rf=0.1 hexane-ethyl acetate (9-1).

EXAMPLE 12

[2-(difluoromethoxy) 4-thiazolyl] methyl [1R-[1α, 3α(Z)]]-3-(2-chloro 3,3,3-trifluoro 1-propenyl) 2,2-dimethyl cyclopropane carboxylate with a Rf=0.3 hexane-methylene chloride (50-50).

PREPARATION OF

12

2-(difluoromethoxy) 4-thiazolemethanol

STAGE A ethyl 2(difluoromethoxy) 4-thiazolecarboxylate

A mixture of 1.2 g of ethyl 2-oxo 4-thiazole-carboxylate, 3 g of potassium carbonate and 10 ml of anhydrous dimethylformamide (DMF) was heated to about 80° C. in the presence of chlorodifluoromethane and once the reaction was complete, the reaction medium was poured into water and extracted with ethyl acetate. The extracts were washed with water, dried and evaporated to dryness to obtain 3 g of a product which was purified by chromatography on silica eluting with a hexane-ethyl acetate mixture (80-20) to obtain 1.2 g of the desired product with a Rf=0.3.

STAGE B 2-(difluoromethoxy) 4-thiazolemethanol 7.2 ml of a 1.5 molar solution of diisobutylaluminium hydride (DIBAL) in toluene were introduced at −60° C. into a mixture of 1.2 g of the product of Stage A and 35 ml of anhydrous toluene and the temperature was allowed to rise to −30° C. The reaction mixture was held at −30° C. for 2 hours and poured into a molar solution of sodium and potassium double tartrate cooled to 0° C. The mixture was stirred for 2 hours at ambient temperature, followed by extraction with ethyl acetate. The extracts were washed with water, dried and brought to dryness to obtain 2.4 g of product which was purified by chromatography on silica and eluting with a hexane-ethyl acetate mixture (50-50) to obtain 840 mg of the desired product with a Rf=0.2, [eluant: hexane-ethyl acetate (50-50)].

EXAMPLE 13

[2-(difluoromethoxy) 4-thiazolyl] methyl [1R1α, 3α(E)]]-3-(3-ethoxy 2-fluoro 3-oxo 1-propenyl) 2,2-dimethyl cyclopropane carboxylate with a Rf=0.25 [hexane-methylene chloride (20-80)].

EXAMPLE 14

1-[2-(difluoromethoxy) 4-thiazolyl] 2-propynyl [1R-[1α, 3α(Z)]]-3-(2-chloro 3,3,3-trifluoro 1-propenyl) 2,2-dimethyl cyclopropane carboxylate with a Rf=0.3 [hexane-methylene chloride (50-50)].

PREPARATION OF EXAMPLE 14

2-(difluoromethoxy) alpha-ethynyl 4-thiazolemethanol a) Preparation of the aldehyde 50 ml of a solution of methylene chloride with 2.47 g of 2-(difluoromethoxy) 4-thiazolemethanol were added to a suspension of 3 g of pyridinium chlorochromate and 50 ml of methylene chloride. The reaction mixture was maintained at 25° C. for 90 minutes and filtered. The methylene chloride was evaporated off and the residue was purified on silica eluting with a hexane-ethyl acetate mixture (50-50) to obtain 2.6 g of the desired product.

b) Ethynylation stage 13 ml of a 0.5M solution in THF of ethynyl magnesium bromide were added at 0° C. to a mixture of 6 mmoles of the product of Stage A and 6 ml of anhydrous THF and the reaction mixture was stirred at 0° C. and then poured into a saturated aqueous solution of ammonium chloride. Extraction was carried out with ethyl acetate and the extracts were washed, dried over magnesium sulfate and evaporated to dryness. The residue was chromatographed on silica, eluting with a hexane-ethyl acetate mixture (70-30) to obtain 720 mg of the desired product with a Rf=0.25 (hexane-ethyl acetate 7-3).

EXAMPLE 15

1-[2-difluoromethoxy-4-thiazolyl] ethyl [1R-[1α, 3α(Z)]]-3-(2-chloro 3,3,3-trifluoro 1-propenyl) 2,2-dimethyl cyclopropane carboxylate Using the procedure of Example 1, the solution prepared hereafter and [1R-(1α, 3α(Z)]-3-(2-chloro 3,3,3-trifluoro 1-propenyl) 2,2-dimethyl cyclopropane carboxylic acid were reacted to obtain the desired product with a Rf=0.3 (eluant: hexane-methylene chloride (70-30)).

PREPARATION OF EXAMPLE 15

1-[2-(difluoromethoxy) 4-thiazolyl] ethanol

A 3M solution of methyl magnesium bromide in THF was added at 0°±5° C. to a solution of 6 mmoles of the aldehyde prepared in Stage a) of the preparation of Example 14 in 15 ml of THF. The reaction mixture was stirred for 15 minutes at 0° C. and poured into a 10% aqueous solution of ammonium chloride. Extraction was carried out with ethyl ether and the extracts were dried over magnesium sulfate to obtain 70 ml of a solution containing the desired alcohol which was used as is in the following stage.

EXAMPLE 16

(4-thiazolyl) methyl [1R-[1α, 3α(Z)]]-3-(2-chloro 3,3,3-trifluoro 1-propenyl) 2,2-dimethyl cyclopropane carboxylate with a Rf=0.08 [hexane-ethyl acetate (9-1)].

EXAMPLE 17

[2-(1-methyl ethyl) 4-thiazolyl] methyl [1R-[1α, 3α(Z)]]-3-(2-chloro 3,3,3-trifluoro 1-propenyl) 2,2-dimethyl cyclopropane carboxylate with a specific rotation of $[\alpha]_D = +19°$ (c=1.3% in $CHCl_3$).

EXAMPLE 18

(2-fluoro 4-thiazolyl) methyl [1R-[1α, 3α(Z)]]-3-(2-chloro 3,3,3-trifluoro 1-propenyl) 2,2-dimethyl cyclopropane carboxylate with a Rf=0.25 [hexane-methylene chloride (50-50)].

PREPARATION OF EXAMPLE 18

2-fluoro 4-thiazolemethanol

STAGE A ethyl 2-fluoro 4-thiazole carboxylate

A suspension of 2.1 g of ethyl 2-chloro 4-thiazole carboxylate, 15 ml of dimethylsulfoxide (DMSO) and 2 g of potassium fluoride was heated to 140° C. for 20 hours and the product was chromatographed, eluting with a hexane-ethyl acetate mixture (80-20) to obtain 0.82 g of the desired product melting at 74° C.

STAGE B 2-fluoro 4-thiazolemethanol

A solution of 600 mg of the product of Stage A and 20 ml of THF was cooled to −60° C. and 4.5 ml of 1.5 molar DIBAL in toluene were introduced at −60° C. The temperature was allowed to rise to −10°/−20° C. and 34 mg of sodium borohydride were added. The mixture was stirred for 30 minutes at 0°/−5° C. and then was poured into a molar solution of sodium and potassium double tartrate. The mixture was stirred for one hour at ambient temperature, followed by extraction with ethyl acetate. The extracts were washed, dried over magnesium sulfate and evaporated to dryness to obtain a residue which was chromatographed and eluted with a hexane-ethyl acetate mixture (50-50) to obtain 450 mg of the desired product with a Rf=0.25.

EXAMPLE 19

(2-phenoxy 4-thiazolyl) methyl [1R-[1α, 3α(Z)]]-3-(2-chloro 3,3,3-trifluoro 1-propenyl) 2,2-dimethyl cyclopropanecarboxylate with a specific rotation of $[\alpha]_D = +16.5°$ (c=1.1% in $CHCl_3$).

EXAMPLE 20

[2-[4-trifluoromethoxy-phenyl] 4-thiazolyl] methyl [1R-[1α, 3α(Z)]]-3-(2-chloro 3,3,3-trifluoro 1-propenyl) 2,2-dimethyl cyclopropane carboxylate with a specific rotation of $[\alpha]_D = +12.5°$ (c=1.15% in $CHCl_3$).

EXAMPLE 21

[2-[3-trifluoromethoxy-phenyl] 4-thiazolyl] methyl [1R-[1α, 3α(Z)]]-3-(2-chloro 3,3,3-trifluoro 1-propenyl) 2,2-dimethyl cyclopropane carboxylate with a specific rotation of $[\alpha]_D = +16.5°$ (c=1% in $CHCl_3$).

EXAMPLE 22

[2-[3-trifluoromethyl-phenyl] 4-thiazolyl] methyl [1R-[1α, 3α(Z)]]-3-(2-chloro 3,3,3-trifluoro 1-propenyl) 2,2-dimethyl cyclopropane carboxylate with a specific rotation of $[\alpha]_D = +14.5°$ (c=1.15% in CHCl$_3$).

EXAMPLE 23

[2-[4-trifluoromethyl-phenyl] 4-thiazolyl] methyl [1R-[1α, 3α(Z)]]-3-(2-chloro 3,3,3-trifluoro 1-propenyl) 2,2-dimethyl cyclopropane carboxylate with a specific rotation of $[\alpha]_D = +14°$ (c=1.2% in CHCl$_3$).

EXAMPLE 24

[2-[2-trifluoromethyl-phenyl] 4-thiazolyl] methyl [1R-[1α, 3α(Z)]]-3-(2-chloro 3,3,3-trifluoro 1-propenyl) 2,2-dimethyl cyclopropane carboxylate with a specific rotation of $[\alpha]_D = +19.5°$ (c=0.85% in CHCl$_3$).

EXAMPLE 25

[2-(2-ethyl 4-thiazolyl) 4-thiazolyl] methyl [1R-[1α, 3α(Z)]]-3-(2-chloro 3,3,3-trifluoro 1-propenyl) 2,2-dimethyl cyclopropane carboxylate with a specific rotation of $[\alpha]_D = +11.5°$ (c=1% in CHCl$_3$).

EXAMPLE 26

(2-chloro 4-thiazolyl) methyl [1R-[1α, 3α(Z)]]-3-(2-chloro 3,3,3-trifluoro 1-propenyl) 2,2-dimethyl cyclopropane carboxylate with a specific rotation of $[\alpha]_D = +24.5°$ (c=1.05% in CHCl$_3$).

EXAMPLE 27

[2-(2-thienyl) 4-thiazolyl] methyl [1R-[1α, 3α(Z)]]-3-(2-chloro 3,3,3-trifluoro 1-propenyl) 2,2-dimethyl cyclopropane carboxylate with a specific rotation of $[\alpha]_D = +14.5°$ (c=1% in CHCl$_3$).

EXAMPLE 28

(2-methylthio 4-thiazolyl) methyl [1R-[1α, 3α(Z)]]-3-(2-chloro 3,3,3-trifluoro 1-propenyl) 2,2-dimethyl cyclopropane carboxylate with a specific rotation of $[\alpha]_D = +20°$ (c=1.05% in CHCl$_3$).

EXAMPLE 29

(2-methyl 4-thiazolyl) methyl [1R-[1α, 3α(Z)]]-3-(2-chloro 3,3,3-trifluoro 1-propenyl) 2,2-dimethyl cyclopropane carboxylate with a Rf=0.14 [hexane-ethyl acetate (9-1)].

EXAMPLE 30

(2-chloro 5-thiazolyl) methyl [1R-[1α, 3α(Z)]]-3-(2-chloro 3,3,3-trifluoro 1-propenyl) 2,2-dimethyl cyclopropane carboxylate with a specific rotation of $[\alpha]_D = +59°$ (c=1.1% in CHCl$_3$).

EXAMPLE 31

(5-thiazolyl) methyl 1R-[1α, 3α(Z)]-3-(2-chloro 3,3,3-trifluoro 1-propenyl) 2,2-dimethyl cyclopropane carboxylate with a specific rotation of $[\alpha]_D = +45°$ (c=1.1% in CHCl$_3$).

EXAMPLE 32

(2-phenoxy 5-thiazolyl) methyl [1R-[1α, 3α(Z)]]-3-(2-chloro 3,3,3-trifluoro 1-propenyl) 2,2-dimethyl cyclopropane carboxylate with a Rf= +14° C. (c=1% in CHCl$_3$).

EXAMPLE 33

(2-phenoxy 5-thiazolyl) methyl [1R-[1α, 3α(E)]]-3-(3-ethoxy 2-fluoro 3-oxo 1-propenyl) 2,2-dimethyl cyclopropane carboxylate with a specific rotation of $[\alpha]_D = +29°$ (c=1% in CHCl$_3$).

EXAMPLE 34

4-thiazolyl-methyl [1R-[1α, 3α(E)]]-3-(3-ethoxy 2-fluoro 3-oxo 1-propenyl) 2,2-dimethyl cyclopropane carboxylate with a Rf=0.13 [hexane-ethyl acetate (8-2)].

EXAMPLE 35

[2-isopropyl-4-thiazolyl] methyl [1R-[1α, 3α(E)]]-3-(3-ethoxy 2-fluoro 3-oxo 1-propenyl) 2,2-dimethyl cyclopropane carboxylate with a Rf=0.29 [hexane-ethyl acetate (8-2)].

EXAMPLE 36

1-(2-methyl 4-thiazolyl) 2-propynyl [1R-[1α, 3α(Z)]]-3-(2-chloro 3,3,3-trifluoro 1-propenyl) 2,2-dimethyl cyclopropane carboxylate with a Rf=0.21 [heptane-ethyl acetate (8-2)].

PREPARATION OF EXAMPLE 36

α-ethynyl 2-methyl 4-thiazolemethanol

Using the procedure of Example 1, 2-methyl-4-thiazolecarboxaldehyde was reacted to obtain the desired product melting at 94° C.

EXAMPLE 37

1-[2-trifluoromethyl-4-thiazolyl] ethyl [1R-[1α, 3α(E)]]-3-(3-ethoxy 2-fluoro 3-oxo 1-propenyl) 2,2-dimethyl cyclopropane carboxylate with a Rf=0.13 [hexane-ethyl acetate (8-2)].

PREPARATION OF EXAMPLE 37

1-[2-(trifluoromethyl) 4-thiazolyl] ethanol

Using the procedure of Example 1, 2-trifluoromethyl-4-thiazolecarboxaldehyde and methyl magnesium bromide were reacted to obtain the desired product with a Rf=0.17 [hexane-ethyl acetate (7-3)].

EXAMPLE 38

1-(2-bromo 4-thiazolyl)-2-propynyl [1R-[1α, 3α(Z)]]-3-(2-chloro 3,3,3-trifluoro 1-propenyl) 2,2-dimethyl cyclopropane carboxylate melting at 76° C.

PREPARATION OF EXAMPLE 38

2-bromo α-ethynyl 4-thiazolemethanol

Using the procedure of Example 1, 2-bromo-4-thiazole carboxaldehyde and ethynyl magnesium bromide were reacted to obtain the desired product with a Rf=0.17 [hexane-ethyl acetate (7-3)].

EXAMPLE 39

(2-bromo 4-thiazolyl) methyl [1R-[1α, 3α(E)]]-3-(3-ethoxy 2-fluoro 3-oxo 1-propenyl) 2,2-dimethyl cyclopropane carboxylate with a Rf=0.11 [heptane-ethyl acetate (9-1)].

PREPARATION OF EXAMPLE 39

2-bromo 4-thiazolemethanol

STAGE A ethyl 2-bromo 4-thiazole carboxylate

A mixture of 15 ml of dichloroethane in a mixture of 2.87 g of phosphorous bromide and 1.73 g of ethyl 2-oxo 4-thiazole carboxylate was refluxed for 4 hours and then poured into a water and ice mixture. Extraction was carried out with methylene chloride and the extracts were dried over magnesium sulfate, filtered and evaporated to dryness. The residue was chromatographed on silica eluting with a hexane-ethyl acetate mixture (7-3) to obtain 1.2 g of the desired product melting at 69° C.

STAGE B 2-bromo 4-thiazolemethanol and 2-bromo 4-thiazolecarboxaldehyde 141 ml of 1.2 molar DIBAL in hexane were added at −60° C. to a solution of 20 g of the product of Stage A and 200 ml of tetrahydrofuran and the reaction mixture was stirred for one hour. The temperature was allowed to rise to −20° C. and the reaction mixture was poured into a molar solution of sodium and potassium double tartrate. Extraction was carried out with ethyl acetate and the extracts were dried, filtered and evaporated to dryness. The residue was chromatographed on silica, eluting with a hexane-ethyl acetate mixture (7-3) to obtain 14.9 g of 2-bromo 4-thiazole methanol (Rf=0.06) and 1 g of 2-bromo 4-thiazole-carboxaldehyde (RF=0.29) melting at 124° C.

EXAMPLE 40

[2-[4-trifluoromethoxy-phenyl] 4-thiazolyl] methyl [1R-[1α, 3α(E)]]-3-(3-ethoxy 2-fluoro 3-oxo 1-propenyl) 2,2-dimethyl cyclopropane carboxylate with a Rf=0.34 [hexane-ethyl acetate (8-2)].

EXAMPLE 41

(2-chloro 4-thiazolyl) methyl [1R-[1α, 3α(E)]]-3-(3-ethoxy 2-fluoro 3-oxo 1-propenyl) 2,2-dimethyl cyclopropane carboxylate with a Rf=0.30 [hexane-ethyl acetate (8-2)].

EXAMPLE 42

(2-methylthio 4-thiazolyl) methyl [1R-[1α, 3α(E)]]-3-(3-ethoxy 2-fluoro 3-oxo 1-propenyl) 2,2-dimethyl cyclopropane carboxylate melting at 76° C.

EXAMPLE 43

1-[2-(trifluoromethyl) 4-thiazolyl] ethyl [1R-[1α, 3α(Z)]]-3-(2-chloro 3,3,3-trifluoro 1-propenyl) 2,2-dimethyl cyclopropane carboxylate with a Rf=0.09 [heptane-ethyl acetate (9-1)].

EXAMPLE 44

(2-bromo 4-thiazolyl) methyl [1R-[1α, 3α(Z)]]-3-(2-chloro 3,3,3-trifluoro 1-propenyl) 2,2-dimethyl cyclopropane carboxylate using the alcohol of example 39 to obtain the desired product with a Rf=0.17 [heptane-ethyl acetate (9-1)].

EXAMPLE 45 cyano [2-trifluoromethyl-4-thiazolyl] methyl [1R-[1α, 3α(Z)]]-3-(2-chloro 3,3,3-trifluoro 1-propenyl) 2,2-dimethyl cyclopropane carboxylate melting at <50° C. and with a Rf=0.32 (hexane-ethyl acetate 8-2).

EXAMPLE 46

[2-(1-fluoro 1-propynyl)-4-thiazolyl] methyl [1R-[1α, 3α(Z)]]-3-(2-chloro 3,3,3-trifluoro 1-propenyl) 2,2-dimethyl cyclopropane carboxylate with a Rf=0.11 [hexane ethyl acetate (8-2)].

PREPARATION OF EXAMPLE 46

2-(1-fluoro 2-propynyl) 4-thiazolemethanol

STAGE A 2-(bromomethyl) 4-[[(tetrahydro 2H-pyran-2-yl) oxy] methyl]-thiazole The product was prepared by reaction of dihydropyran and the alcohol of the desired product to obtain the latter with a Rf=0.46 [hexane-ethyl acetate (1-1)].

STAGE B

4-[[(tetrahydro 2H-pyran-2-yl) oxy] methyl] 2-thiazole carboxaldehyde

A mixture of 5 g of the product of Stage A, 50 ml of methylene chloride and 9.5 g of monohydrated N-oxide N-methyl morpholine was stirred at 20° C. for one hour and the product was evaporated to dryness, then chromatographed on silica eluting with a cyclohexane-ethyl acetate mixture (7-3) to obtain 2.8 g of the desired product with a Rf=0.27.

STAGE C

α-ethynyl 4-[[(tetrahydro 2H-pyran-2-yl) oxy] methyl] 2-thiazole methanol

The product was prepared starting with the product of Stage B and ethynyl magnesium bromide using the procedure of Example 1 to obtain the desired product with a Rf=0.11 (hexane-ethyl acetate (7-3)).

STAGE D

2-(1-fluoro 2-propynyl)-4-thiazolemethanol 0.53 ml of diethylaminosulfide trifluoride (DAST) were added at about −60° C. to a solution of 1 g of the product of Stage C and 5 ml of methylene chloride and the reaction mixture was stirred for 2 hours at −55° C. and poured into a solution of sodium bicarbonate. Extraction was carried out with methylene chloride and the extracts were dried over magnesium sulfate, filtered and evaporated to dryness. The residue was taken up in 5 ml of methanol and 20 mg of toluene-sulfonic acid were added. The reaction mixture was stirred for one hour at 20° C., followed by evaporation to dryness. The residue was chromatographed on silica eluting with a hexane-ethyl acetate mixture (7-3) to obtain 0.16 g of the desired product with a Rf=0.10.

EXAMPLE 47

1-(methylthio 4-thiazolyl) 2-propynyl 1R[1α, 3α(Z)] 2,2-dimethyl 3-(3,3,3-trifluoro 2-chloropropenyl) cyclopropane carboxylate with a Rf=0.16 (heptane-AcOEt 8-2).

PREPARATION OF EXAMPLE 47

2-methylthio-α-ethynyl 4-thiazol methanol.

Ethyl 2-chloro 4-thiazol carboxylate was reacted with sodium thiomethoxide in the presence of sodium borohydride to obtain 2-methylthio 4-thiazolyl methanol which was treated with manganese dioxide to obtain the corresponding aldehyde, then with ethynyl magnesium bromide as in Example 14 to obtain the expected alcohol.

EXAMPLE 48

1-(2-methylthio 4-thiazolyl) 2-propynyl [1R-[1α, 3α(E)]] 3-(3-ethoxy 2-fluoro 3-oxo 1-propenyl) 2,2-dimethyl cyclopropane carboxylate with a Rf=0.13 (heptane-AcOEt 8-2).

EXAMPLE 49

1-(2-fluoro 4-thiazolyl) 2-propynyl 1R[1α,3α, (Z)] 2,2-dimethyl 3-(3,3,3-trifluoro 2-chloropropenyl) cyclopropane carboxylate with a Rf=0.2 [CH$_2$Cl$_2$-hexane 5-5].

PREPARATION OF EXAMPLE 49

2-fluoro-α-ethynyl 4-thiazol methanol.

Using the procedure of Example 14, the alcohol of Example 18 was reacted to obtain the expected product.

EXAMPLE 50

1-(2-chloro 4-thiazolyl)-2-propynyl 1R[1α, 3α(Z)] 2,2-dimethyl 3-(3,3,3-trifluoro 2-chloropropenyl) cyclopropane carboxylate with a Rf=0.2 (CH$_2$Cl$_2$-heptane 5-5).

PREPARATION OF EXAMPLE 50

2-chloro-α-ethynyl 4-thiazol methanol.

Ethyl 2-chloro 4-thiazol carboxylate was reacted with sodium borohydride in the presence of methanol to obtain the corresponding aldehyde, then with ethynyl magnesium bromide as in example 14 to obtain the expected alcohol.

EXAMPLE 51

1-(2-chloro 4-thiazolyl) ethyl 1R[1α, 3α(Z)] 2,2-dimethyl 3-(3,3,3-trifluoro 2-chloropropenyl) cyclopropane carboxylate with a Rf=0.2 (CH$_2$Cl$_2$-heptane 5-5).

EXAMPLE 52

1-(2-ethynyl 4-thiazolyl) methyl 1R[1α, 3α(Z)] 2,2-dimethyl 3-(3,3,3-trifluoro 2-chloropropenyl) cyclopropane carboxylate with a Rf=0.2 (CH$_2$Cl$_2$-heptane 8-2).

PREPARATION OF EXAMPLE 52

2-ethynyl 4-thiazol methanol.

2-bromo 4-thiazolyl methanol of preparation 39 was reacted with trimethylacetylene in the presence of copper iodide, bis(triphenylphosphine) palladium chloride and triethylamine and then the mixture was poured into an aqueous solution of ammonium chloride to obtain the expected alcohol.

EXAMPLE 53

1-(2-ethynyl 4-thiazolyl) 2-propynyl 1R[1α, 3α(Z)] 2,2-dimethyl 3-(3,3,3-trifluoro 2-chloropropenyl) cyclopropane carboxylate with a Rf approx. 0.2 (heptane-CH$_2$Cl$_2$ 4-6).

PREPARATION OF EXAMPLE 53

2-ethynyl α-ethynyl 4-thiazol methanol.

Using the procedure of preparation 14, the alcohol of example 52 was reacted to obtain the expected alcohol.

EXAMPLE 54

R and S cyano methyl 1-(2-chloro 4-thiazolyl) 1R[1α, 3α(Z)] 2,2-dimethyl 3-(3,3,3-trifluoro 2-chloropropenyl) cyclopropane carboxylate with a Rf=0.25 (CH$_2$Cl$_2$-heptane 7-3).

EXAMPLE 55

1-(2-bromo 4-thiazolyl) 2-propynyl [1R-[1α, 3α(E)]] 3-(3-ethoxy 2-fluoro 3-oxo 1-propenyl) 2,2-dimethyl cyclopropane carboxylate with a Rf=0.19 (heptane-AcOEt 9-1).

EXAMPLE 56

[2-(pentafluoroethyl)-4-thiazolyl] methyl 1R[1α, 3α(Z)] 2,2-dimethyl 3-(3,3,3-trifluoro 2-chloropropenyl) cyclopropane carboxylate with a Rf=0.14 (heptane-CH$_2$Cl$_2$ 7-3).

PREPARATION OF EXAMPLE 56

2-pentafluoroethyl 4-thiazol methanol and 2-pentafluoroethyl 4-thiazol carboxaldehyde.

Ethyl bromopyruvate was reacted with pentafluoropropane thioamide in ethanolic medium to obtain ethyl 2-pentafluoroethyl 4-thiazol carboxylate which was reacted as in Stage B of preparation 39 to obtain the expected products.

EXAMPLE 57

1-[2-(pentafluoroethyl) 4-thiazolyl) 2-propynyl-1R[1α, 3α(Z)] 2,2-dimethyl 3-(3,3,3-trifluoro 2-chloropropenyl) cyclopropane carboxylate with a Rf=0.12 (heptane-AcOEt 9-1).

PREPARATION OF EXAMPLE 57

2-pentafluoroethyl α-ethynyl 4-thiazol methanol.

Using the procedure of preparation 1, the product of the preparation of example 56 was reacted to obtain the expected alcohol.

EXAMPLE 58

1-(2-difluoromethoxy) 4-thiazolyl) 2-propynyl R[1α, 3α(E)] 3-(2-fluoro 3-methoxy 3-oxo 1-propenyl) 2,2-dimethyl cyclopropane carboxylate.

PREPARATION OF EXAMPLE 58

2-(difluoromethyl) α-ethynyl 4-thiazol methanol.

Using the procedure of preparation 1, 2-(difluoromethyl)-4-thiazol carboxaldehyde was reacted to obtain the expected alcohol.

EXAMPLE 59

(2-difluoromethyl) 4-thiazolyl) methyl 1R[1α, 3α(Z)] 2,2-dimethyl 3-(3,3,3-trifluoro 2-chloropropenyl) cyclopropane carboxylate with a Rf=0.12 (heptane-AcOEt 95-5).

EXAMPLE 60

(2-difluoromethyl) 4-thiazolyl) methyl 1R[1α, 3α(E)] 3-(2-fluoro 3-methoxy 3-oxo 1-propenyl) 2,2-dimethyl cyclopropane carboxylate with a Rf=0.10 (heptane-AcOEt 95-5).

EXAMPLE 61

1-(2-difluoromethyl) 4-thiazolyl) 2-propynyl 1R[1α, 3α(E)] 3-(2-fluoro 3-methoxy 3-oxo 1-propenyl) 2,2-dimethyl cyclopropane carboxylate with a Rf=0.11 (heptane-CH$_2$Cl$_2$ 4-6).

EXAMPLE 62

1-(2-difluoromethyl) 4-thiazolyl) 2-propynyl 1R[1α, 3α(Z)] 2,2-dimethyl 3-(3,3,3-trifluoro 2-chloropropenyl) cyclopropane carboxylate with a Rf=0.12 (heptane-CH$_2$Cl$_2$ 5-5).

EXAMPLE 63

(3-difluoromethyl) 2-oxo 5-thiazolyl) methyl 1R[1α, 3α(Z)] 2,2-dimethyl 3-(3,3,3-trifluoro 2-chloropropenyl) cyclopropane carboxylate with a Rf=0.19 (heptane-CH$_2$Cl$_2$ 1-1).

PREPARATION OF EXAMPLE 63

2-oxo 3-difluoromethyl) 5-thiazol methanol and the corresponding 4,5-dihydro product.

A solution of methyl 2-oxo 5-thiazol carboxylate in dimethylformamide in the presence of potassium carbonate was heated at 80° C. and reacted with Freon 22 to obtain methyl 2-oxo 3-(difluoromethyl) 5-thiazol carboxylate which was treated with sodium borohydride in the presence of methanol to obtain the expected alcohol.

EXAMPLE 64

[2-(pentafluoroethyl) 4-thiazolyl) methyl 1R[1α, 3α(E)] 3-(2-fluoro 3-methoxy 3-oxo 1-propenyl) 2,2-dimethyl cyclopropane carboxylate with a Rf=0.11 (heptane-AcOEt 8-2).

EXAMPLE 65

(3-difluoromethyl 2-oxo 5-thiazolyl) methyl 1R[1α, 3α(E)] 3-(2-fluoro 3-methoxy 3-oxo 1-propenyl) 2,2-dimethyl cyclopropane carboxylate.

EXAMPLE 66

2-oxo 3-difluoromethyl 4,5-dihydro (3H)-5-thiazolyl methyl 1R[1α, 3α(E)] 3-(2-fluoro 3-methoxy 3-oxo 1-propenyl) 2,2-dimethyl cyclopropane carboxylate with a Rf=0.15 (hexane-AcOEt 8-2).

EXAMPLE 67

1-(3-difluoromethyl) 2-oxo 5-thiazolyl) 2-pyridyl R[1α, 3α(Z)] 2,2-dimethyl 3-(3,3,3-trifluoro 2-chloropropenyl) cyclopropane carboxylate with a Rf=0.09 (heptane-CH$_2$Cl$_2$ 5-5).

PREPARATION OF EXAMPLE 67

2-oxo 3-(difluoromethyl) α-ethynyl 5-thiazol methanol.

Using the procedure of example 14, the alcohol of the preparation of example 63 was reacted to obtain the expected alcohol.

EXAMPLE 68

(2-trifluoromethyl) 5-thiazolyl) methyl 1R[1α, 3α(Z)] 2,2-dimethyl 3-(3,3,3-trifluoro 2-chloropropenyl) cyclopropane carboxylate.

EXAMPLE 69

1-(2-trifluoromethyl) 5-thiazolyl) 2-pyridinyl 1R[1α, 3α(Z)] 2,2-dimethyl 3-(3,3,3-trifluoro 2-chloropropenyl) cyclopropane carboxylate with a Rf=0.2 (heptane-CH$_2$Cl$_2$ 5-5).

PREPARATION OF EXAMPLE 69

2-trifluoromethyl α-ethynyl 5-thiazol methanol.

Using the procedure of preparation 1, 2-trifluoromethyl 5-thiazol carboxaldehyde was reacted to obtain the expected alcohol.

EXAMPLE 70

(2-difluoromethylthio) 4-thiazolyl) methyl 1R[1α, 3α(Z)] 2,2-dimethyl 3-(3,3,3-trifluoro 2-chloropropenyl) cyclopropane carboxylate with a Rf=0.14 (heptane-CH$_2$Cl$_2$ 5-5).

EXAMPLE 71

1-(2-trifluoromethyl 4-thiazolyl) 2-propynyl 1R[1α, 3α] 3-(2,2-dichloroethenyl) 2,2-dimethyl cyclopropane carboxylate with a Rf=0.14 (heptane-CH$_2$Cl$_2$ 5-5).

EXAMPLE 72

1-(2-trifluoromethyl 4-thiazolyl)-2-propynyl 1R[1α, 3α(Z+E)] 2-chloro 2-fluoroethenyl) 2,2-dimethyl cyclopropane carboxylate with a Rf=0.11 (heptane-CH$_2$Cl$_2$ 5-5).

EXAMPLE 73

(2-trifluoromethyl 4-thiazolyl) ethenyl 1R[1α, 3α(Z)] 2,2-dimethyl 3-(3,3,3-trifluoro 2-chloropropenyl) cyclopropane carboxylate.

EXAMPLE 74

1-(2-trifluoromethyl 4-thiazolyl) 2-propynyl 1R[1α, 3α(Z)] 3-(2-methyl 1-propenyl) 2,2-dimethyl cyclopropane carboxylate with a Rf=0.24 (heptane-tBuOCH$_3$ 9-1).

EXAMPLE 75

1-(2-trifluoromethyl 4-thiazolyl) 2-propynyl 1R[1α, 3α] 3-(2,2-difluoroethenyl) 2,2-dimethyl cyclopropane carboxylate with a Rf=0.22 (heptane-tBuOCH$_3$ 9-1).

EXAMPLE 76

1-(2-trifluoromethyl 4-thiazolyl) 2-propynyl 1R[1α, 3β(Z)] 3-(2-fluoro 3-methoxy 3-oxo 1-propenyl) 2,2-dimethyl cyclopropane carboxylate with a Rf=0.23 (heptane-AcOEt 7-3).

EXAMPLE 77

1-(2-trifluoromethyl 4-thiazolyl) 2-propynyl 1R[1α, 3α(Z)] 3-(3-oxo 3-(2-trifluoromethoxy 1-propenyl) 2,2-dimethyl cyclopropane carboxylate with a Rf=0.19 (heptane-CH$_2$Cl$_2$ 5-5).

EXAMPLE 78

(2-trifluoromethyl 5-thiazolyl) methyl 1R[1α, 3α(E)] 3-(2-fluoro 3-methoxy 3-oxo 1-propenyl) 2,2-dimethyl cyclopropane carboxylate with a Rf=0.24 (heptane-AcOEt 7-3).

EXAMPLE 79

1-[2-(1-methylethyl) 4-thiazolyl] 2-propynyl 1R[1α, 3α(Z)] 2,2-dimethyl 3-(3,3,3-trifluoro 2-chloropropenyl) cyclopropane carboxylate with a Rf=0.26 (heptane-AcOEt 9-1).

PREPARATION OF EXAMPLE 79

2-(isopropyl) α-ethynyl 4-thiazol methanol.

Using the procedure of example 56, thioisobutyramide was reacted to obtain 2-(isopropyl) ethyl 4-thiazolyl carboxylate which was reacted with methanol and sodium borohydride to obtain 2-(isopropyl) 4-thiazol methanol which was treated with manganese dioxide to obtain the corresponding aldehyde which was reacted as in stage B of the preparation of example 14 to obtain the expected product.

EXAMPLE 80

1-(2-difluoromethoxy 4-thiazolyl) 2-propynyl 1R[1α, 3α(E)] 3-(2-fluoro 3-methoxy 3-oxo 1-propenyl) 2,2-dimethyl cyclopropane carboxylate with a Rf=0.10 (heptane-isopropyl ether 9-1).

EXAMPLE 81

1-(2-isopropyl 4-thiazolyl) 2-propynyl 1R[1α, 3α(E)] 3-(2-fluoro 3-methoxy 3-oxo 1-propenyl) 2,2-dimethyl cyclopropane carboxylate with a Rf=0.20 (heptane-AcOEt 8-2).

EXAMPLE 82

1-(2-difluoromethoxy 4-thiazolyl) 2-propynyl 1R[1α, 3α] 3-(2,2-dichloroethenyl) 2,2-dimethyl cyclopropane carboxylate.

EXAMPLE 83

1-(2-difluoromethoxy 4-thiazolyl) 2-propynyl 1R[1α, 3α] 3-(2,2-difluoroethenyl) 2,2-dimethyl cyclopropane carboxylate.

EXAMPLE 84

1-(2-difluoromethoxy 4-thiazolyl) 2-propynyl 1R[1α, 3α(Z+E)] 3-(2-chloro 2-fluoro ethenyl) 2,2-dimethyl cyclopropane carboxylate.

EXAMPLE 85

(2-bromo 3-trifluoromethyl 5-thiazolyl) ethyl 1R[1α, 3α(Z)] 3-(2-chloro 3,3,3-trichloro 1-propenyl) 2,2-dimethyl cyclopropane carboxylate.

EXAMPLE 86

(2-bromo 3-trifluoromethyl 5-thiazolyl) methyl 1R[1α, 3α(Z)] 3-(2-chloro 3,3,3-trichloro 1-propenyl) 2,2-dimethyl cyclopropane carboxylate.

EXAMPLE 87

A soluble concentrate

A homogeneous mixture of the following was prepared:

| | |
|---|---|
| Product of Example 1: | 0.25 g |
| Piperonyl butoxide: | 1.00 g |
| Tween 80: | 0.25 g |
| Topanol A: | 0.1 g |
| Water: | 98.4 g |

EXAMPLE 88

An emulsifiable concentrate

The following were intimately mixed:

| | |
|---|---|
| Product of Example 1: (isomer B) | 0.015 g |
| Piperonyl butoxide: | 0.5 g |
| Topanol A: | 0.1 g |
| Tween 80: | 3.5 g |
| Xylene: | 95.885 g |

EXAMPLE 89

An emulsifiable concentrate

A homogeneous mixture of the following was made:

| | |
|---|---|
| Product of Example 1: | 1.5 g |
| Tween 80: | 20.00 g |
| Topanol A: | 0.1 g |
| Xylene: | 78.4 g |

EXAMPLE 90

Preparation of granules

Granules were prepared containing 0.1% to 5% of active substances.

BIOLOGICAL STUDY

A—Activity on Diabrotica

The test insects were final-stage larvae of Diabrotica.

A 9 cm diameter disc of filter paper, placed on the bottom of a Petri dish, was treated with 2 ml of an acetonic solution of the product to be tested. After drying, 10 larvae per dose were deposited and the mortality check was carried out 24 hours after the treatment. From a dose of 5 ppm, the products of the invention showed a good activity, notably the products of Examples 1, 62, 71, 72, 75, 83 and 84.

B—Study of the knock-down effect on a housefly

The test insects were 4-day old female houseflies and the test was carried out by spraying in a Kearns and March chamber using a mixture of acetone (5%) and Isopar L (petroleum solvent) as solvent (quantity of solvent used: 2 ml per second). 50 insects per treatment were used. Checks were carried out every minute up to 10 minutes, then after 15 minutes and the KT 50 was determined by the usual methods. At a dose of 1 g/l, the products of the invention showed a good activity.

C—Study of the lethal effect on a housefly

The test insects were 4- to 5-day old female houseflies and the operation was carried out by topical application of 1 microliter of acetone solution of the product to be tested on the dorsal thorax of the insects using an Arnold micromanipulator. 50 individuals per treatment were used and the mortality check was carried out twenty-four hours after treatment. At a dose of 10 mg/l, the product of Example 1 showed a good activity.

Various modifications of the products and method of the invention may be made without departing from the spirit or scope thereof and it is understood that the invention is to be limited only as defined in the appended claims.

What we claim is:

1. A compound in all possible stereoisomer forms and mixtures thereof of the formula

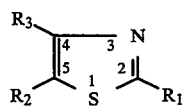

wherein $R_3$ is:

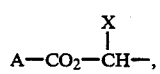

$R_2$ is hydrogen, $R_1$ is selected from the group consisting of alkyl, alkoxy and alkylthio of 1 to 4 carbon atoms optionally substituted by at least one halogen X is methyl or ethynyl and either A is:

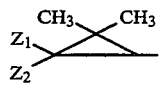

wherein $Z_1$ is hydrogen and either $Z_2$ is:

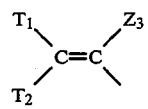

wherein $Z_3$ is hydrogen or halogen and $T_1$ is selected from the group consisting of hydrogen, halogen, alkoxy and alkyl of 1 to 8 carbon atoms optionally substituted by a member of the group consisting of halogen, mono-, di- or trifuluoromethyl, cyano and phenyl optionally substituted by halogen and $T_2$ is selected from the group consisting of hydrogen, halogen, alkoxy of 1 to 8 carbon atoms optionally substituted by halogen or alkyl of 1 to 8 carbon atoms substituted by a member of the group consisting of halogen, mono-, di- or trifluoromethyl, cyano and phenyl optionally substituted by halogen or $T_1$ and $T_2$ form together a cycloalkyl of 3 to 6 carbon atoms or:

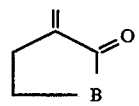

wherein B is oxygen or sulfur;

or $Z_2$ is:

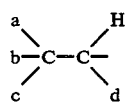

wherein a, b, c and d, individually are halogen or $Z_2$ is:

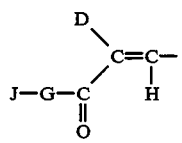

wherein D is selected from the group consisting of hydrogen or halogen, alkoxy of 1 to 8 carbon atoms, G is oxygen or sulfur and J is optionally unsaturated alkyl or cycloalkyl of up to 8 carbon atoms or A is:

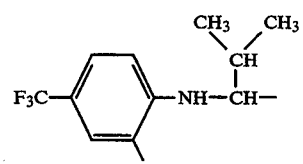

or:

-continued

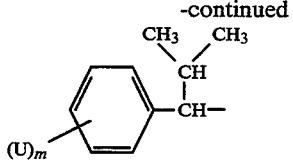

wherein U in any position on the benzene is selected from the group consisting of halogen, alkyl of 1 to 8 carbon atoms and alkoxy of 1 to 8 carbon atoms, m is 0, 1 or 2 and when m is 2, the U substituents may be different and the other two of $R_1$, $R_2$ and $R_3$ which are not:

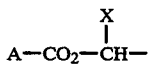

are individually selected from the group consisting of hydrogen, halogen, alkyl, alkenyl and alkynyl of up to 8 carbon atoms optionally substituted by at least one halogen, hydroxyl, O-alkyl, O-alkenyl or O-alkynl, $CO_2$-alkyl, $CO_2$-alkenyl, $CO_2$-alkenyl, $S(O)_n$-alkyl, $S(O)_n$-alkenyl or $S(O)_n$-alkynyl, n is 0, 1 or 2, of up to 8 carbon atoms optionally substituted by at least one halogen, aryl, O-aryl or thioaryl of up to 14 carbon atoms optionally substituted by at least one member of the group consisting of halogen, alkyl, alkenyl and alkynyl of up to 8 carbon atoms optionally substituted by at least one halogen and esterified, etherified or free hydroxy, heteroaryl and heeteroaryloxy, C≡N, $NH_2$ and $NO_2$.

2. A compound of claim 1 wherein $R_2$ is selected from the group consisting of alkyl, O-alkyl and S-alkyl of 1 to 4 carbon atoms substituted by at least one fluorine.

3. A compound of claim 1 wherein one of $R_2$ is —$CF_3$.

4. A compound of claim 1 wherein one of $R_2$ is —$OCHF_2$.

5. A compound of claim 1 wherein X is ethynyl.

6. An insecticidal composition comprising an insecticidally effective amount of at least one compound of claim 1 and an inert carrier.

7. A composition of claim 6 also containing at least one other compound selected from the group consisting of: esters of allethrolone, of 3,4,5,6-tetrahydrophthalimidomethyl alcohol, of 5-benzyl-3-furyl methyl alcohol, of 3-phenoxybenzyl alcohol and of α-cyano-3-phenoxybenzyl alcohol with chrysanthemic acids, by the esters of 5-benzyl-3-furyl methyl alcohol with 2,2-dimethyl-3-(2-oxo-3-tetrahydrothiophenylidenemethyl)-cyclopropane carboxylic acids, by the esters of 3-phenoxybenzyl alcohol and of α-cyano-3-phenoxybenzyl alcohol with 2,2-dimethyl-3-(2,2-dichlorovinyl)-cyclopropane carboxylic acids, by the esters of α-cyano-3-phenoxy-benzyl alcohol with 2,2-dimethyl-3-(2,2-dibromovinyl)-cyclopropane carboxylic acids, by the esters of 3-phenoxybenzyl alcohol with 2-para-chlorophenyl-2-isopropyl acetic acids, by the esters of allethrolone, of 3,4,5,6-tetrahydrophthalimidomethyl alcohol, of 5-benzyl-3-furyl methyl alcohol, of 3-phenoxybenzyl alcohol, and of α-cyano-3-phenoxybenzyl alcohol with 2,2-dimethyl-3-(1,2,2,2-tetrahaloethyl)-cyclopropane carboxylic acids, in which "halo" is fluorine, chlorine or bromine, it being understood that the acid and alcohol copulas of the above pyrethrinoid can exist in all their possible stereoisomer forms.

8. A method of combatting insects comprising contacting insects with an insecticidally effective amount of at least one compound of claim 1.

9. A method of claim 8 wherein the insects are Diabrotica or other soil pesticides.

10. A method of combatting parasites of vegetation, premises or warm-blooded animals comprising contacting such parasites with a parasiticidally effective amount of at least one compound of claim 1.

11. The method of claim 8 wherein the active compound is -1-[2-trifluoromethyl 4-thiazolyl] 2-propynyl [1R-[1α, 3α(Z)]]-3-(2-chloro 3,3,3-trifluoro 1-propenyl) 2,2-dimethyl cyclopropane carboxylate.

* * * * *